(12) United States Patent
Wu et al.

(10) Patent No.: US 10,151,713 B2
(45) Date of Patent: Dec. 11, 2018

(54) X-RAY REFLECTOMETRY APPARATUS FOR SAMPLES WITH A MINISCULE MEASUREMENT AREA AND A THICKNESS IN NANOMETERS AND METHOD THEREOF

(71) Applicants: Industrial Technology Research Institute, Hsinchu (TW); Taiwan Semiconductor Manufacturing Co., Ltd., Hsinchu (TW)

(72) Inventors: Wen-Li Wu, Hsinchu (TW); Yun-San Chien, Kaohsiung (TW); Wei-En Fu, Taoyuan (TW); Shyh-Shin Ferng, Hsinchu (TW); Yi-Hung Lin, Hsinchu (TW)

(73) Assignees: INDUSTRIAL TECHNOLOGY RESEARCH INSTITUTE, Hsinchu (TW); TAIWAN SEMICONDUCTOR MANUFACTURING CO., LTD., Hsinchu (TW)

( * ) Notice: Subject to any disclaimer, the term of this patent is extended or adjusted under 35 U.S.C. 154(b) by 301 days.

(21) Appl. No.: 15/161,046

(22) Filed: May 20, 2016

(65) Prior Publication Data
US 2016/0341674 A1 Nov. 24, 2016

(51) Int. Cl.
*G01N 23/20* (2018.01)
*G01B 15/08* (2006.01)

(52) U.S. Cl.
CPC .............. *G01N 23/20* (2013.01); *G01B 15/08* (2013.01); *G01B 2210/56* (2013.01)

(58) Field of Classification Search
CPC ...... G01N 23/00; G01N 23/20; G01N 23/083; G01N 23/20008; G01N 23/04; G01B 15/02

USPC .............................................. 378/70, 88, 89
See application file for complete search history.

(56) References Cited

U.S. PATENT DOCUMENTS

| 6,711,232 B1 | 3/2004 | Janik |
| 6,754,305 B1 | 6/2004 | Rosencwaig |
| 7,039,158 B1 | 5/2006 | Janik |
| 7,139,365 B1 | 11/2006 | Janik |

(Continued)

FOREIGN PATENT DOCUMENTS

| DE | 4137673 | 5/1993 |
| WO | WO 0196841 | 12/2001 |

OTHER PUBLICATIONS

IOP Publishing, Filatova et al., "Investigation of the structure of thin HfO2 films by soft x-ray reflectometry techniques," Mar. 31, 2009, (8 Pages).

(Continued)

*Primary Examiner* — Jurie Yun
(74) *Attorney, Agent, or Firm* — Nixon Peabody LLP

(57) ABSTRACT

This application relates to an apparatus and methods for enhancing the performance of X-ray reflectometry (XRR) when used in characterizing thin films and nanostructures supported on a flat substrate. In particular, this application is targeted for addressing the difficulties encountered when XRR is applied to samples with very limited sampling volume, i.e. a combination of small sampling area and miniscule sample thickness or structure height. Point focused X-ray with long wavelength, greater than that from a copper anode or 0.154 nm, is preferably used with appropriately controlled collimations on both incident and detection arms to enable the XRR measurements of samples with limited volumes.

18 Claims, 3 Drawing Sheets

(56) References Cited

U.S. PATENT DOCUMENTS 8,422,633 B2  4/2013 Lantz
2015/0247811 A1  9/2015 Yun

OTHER PUBLICATIONS

Applied Physics Letters 87, Lee et al., "Nanoimprint pattern transfer quality from specular x-ray reflectivity," Dec. 27, 2005, (4 Pages).
Applied Physics Letters 93, Cen et al., "Annealing effect on the optical properties of implanted silicon in a silicon nitride matrix," Jul. 17, 2008, (4 Pages).
Journal of Applied Physics Letter 105, Pal et al., "Real-time studies of surface roughness development and reticulation mechanism of advanced photoresist materials during plasma processing," Jan. 12, 2009, (10 Pages).
ECS Transactions 34 (1), Lee et al., "Determining coherence length of x-ray beam using line grating structures," 2011, (6 Pages).
J. Chem. Phys. 101 (5), Wen-li Wu, "Off-specular reflection from flat interfaces," May 9, 1994, (7 Pages).
W.H. Freeman and Company, Guinier, "X-Ray diffraction in crystals, imperfect crystals, and amorphous bodies," 1963, (379 Pages).

X-RAY REFLECTOMETRY APPARATUS FOR SAMPLES WITH A MINISCULE MEASUREMENT AREA AND A THICKNESS IN NANOMETERS AND METHOD THEREOF

CROSS-REFERENCE TO RELATED APPLICATIONS

This non-provisional application claims benefit under 35 U.S.C. § 119(e) to U.S. Provisional Application No. 62/165,051 filed on May 21, 2015, the entire content of which are hereby incorporated by reference.

TECHNICAL FIELD

The application relates generally to an XRR apparatus and a method applicable for samples with a miniscule measurement area and/or with ultrathin thickness or height.

BACKGROUND

X-ray reflectometry (XRR) is a powerful technique to investigate surfaces and interfaces including their roughness, diffuseness across buried layers and thickness of single layer and multilayer stacks by depth profiling the electron density in the direction normal to the sample surface with a sub-nanometer resolution. It has also been shown that XRR is capable of quantifying the cross section profile of surface patterns, for example, in "Nano-imprint pattern transfer quality from specular x-ray reflectivity" by H. J. Lee et al. (APL, 2005), the cross section of line gratings fabricated by nano-imprint as well as the molds used to imprint the patterns have been measured via XRR. A similar application of XRR for measuring nanostructured surfaces has also been documented in U.S. Pat. No. 6,754,305. The efficacy and the limit of the application of XRR to nanoscale surface patterns are based on the effective medium approximation (EMA) as illustrated previously in "Determining Coherence Length of X-ray Beam Using Line Grating Structures" by H. J. Lee et al. (ECS Transactions, 2011). It should be noted that the equivalent concept of EMA has been used in estimating effective refractive index of porous material for ellipsometry or optical scatterometry as illustrated in "Annealing effect on the optical properties of implanted silicon in a silicon nitride matrix" by Z. H. Chen et al. (APL, 2008) and "Real-time studies of surface roughness development and reticulation mechanism of advanced photoresist materials during plasma processing" by A. R. Pal et al. (APL, 2009). The validity of EMA for nanostructures depends on the coherence length of the incident X-ray; only when the coherence length is greater than the lateral characteristic length of the nanostructure along the direction of interest EMA becomes applicable. In such cases, the structure space ratio at any given depth along the surface normal can be deduced from the XRR results. In summary, XRR can be used to measure film thickness as well as the cross sectional shape of nanostructures when the incidence X-ray possesses sufficient coherence length along the direction of interest.

In conventional XRR measurements, for examples, those described in U.S. Pat. No. 6,754,305, U.S. Pat. No. 7,039,158, and U.S. Pat. No. 6,711,232, a wavelength at 0.154 nm from a copper anode is often the preferred choice for measuring film structure; the typical angular range of measurements using X-ray of this wavelength is often between 0° to ~4°. The footprint of X-ray will likely be in the millimeter range due to the low grazing incident angle involved, even for the cases that the incident X-ray is highly focused on the sample. The known focusing techniques such as described in U.S. Pat. No. 6,711,232 and DE 4,137,673 include the use of focusing mirror, curved monochromator and a combination of both. To further limit the size of the incident beam footprint on samples a blocking barrier has been proposed in U.S. Pat. No. 6,711,232. However, by placing a block barrier in the proximity of the sample surface can reduce the total incident beam flux and also inevitably introduce parasitic scatterings from the barrier edge. Both of the abovementioned side effects will serve to deteriorate the signal-to-noise ratio (SNR) of the measured reflection intensities. The characteristic reflection peaks from sample with a thickness of few nanometers are located at high q region where the reflectivity is intrinsically low, typically in $10^{-5}$ or below. In order to acquire signal at high q region with a sufficient SNR the measurement time can be prohibitively long for many applications given that the background noise of the detector is much lower than the weak signal. This low reflectivity or long data acquisition time coupled with a miniscule sample area will render the XRR measurement very challenging. The purpose of this invention is to address the abovementioned challenges and concurrently maintain a reasonable level of SNR as well as certain intricate features of the reflectivity and the q resolution in terms of $\delta q/q$.

SUMMARY

In one embodiment of this application, an X-ray reflectometry (XRR) apparatus includes an X-ray source, an X-ray reflector, a set of incident slits, an X-ray detector and a set of detector slits. The X-ray source is used for emitting an X-ray with a wavelength larger than 0.154 nanometers. The X-ray reflector is used for point focusing the X-ray onto a sample surface at all incident angles involved. The set of incident slits is located between the X-ray reflector and the sample and used for adjusting the incident angle opening of the X-ray. The X-ray detector is used for detecting the X-ray reflected by the surface. The set of detector slits is located between the X-ray detector and the sample and is used for adjusting angle opening of the reflected X-ray collected by the detector. The incident angle is scanned over a preset angular range while both the incident and the detector slits are adjusted continuously to optimize the detected X-ray intensity and the resolution at each scanned angle. In general, the detector slit opening is kept in sync with the incident slit opening; for the present case with an X-ray beam point focused on the sample surface the detector slit opening shall stay close to that of the incident slit in terms of their angular openings.

In one embodiment of the application, a method for XRR includes the steps of: point focusing an X-ray with a wavelength larger than 0.154 nm onto a surface of a sample at a preset incident angle; adjusting the incident angle opening of the X-ray to control the footprint size of the incident X-ray on the sample surface and the resolution of the reflectivity while keeping a maximal allowable X-ray flux on the sample; adjusting the detector angle opening of the reflected X-ray to collect all the specularly reflected X-ray from the sample; and analyzing the XRR data to obtain the structure information of the sample.

BRIEF DESCRIPTION OF THE DRAWINGS

The present application will become more fully understood from the detailed description given herein below and the accompanying drawings which are given by way of illustration only and thus are not limitative of the present application and wherein.

DETAILED DESCRIPTION

Figure 1:
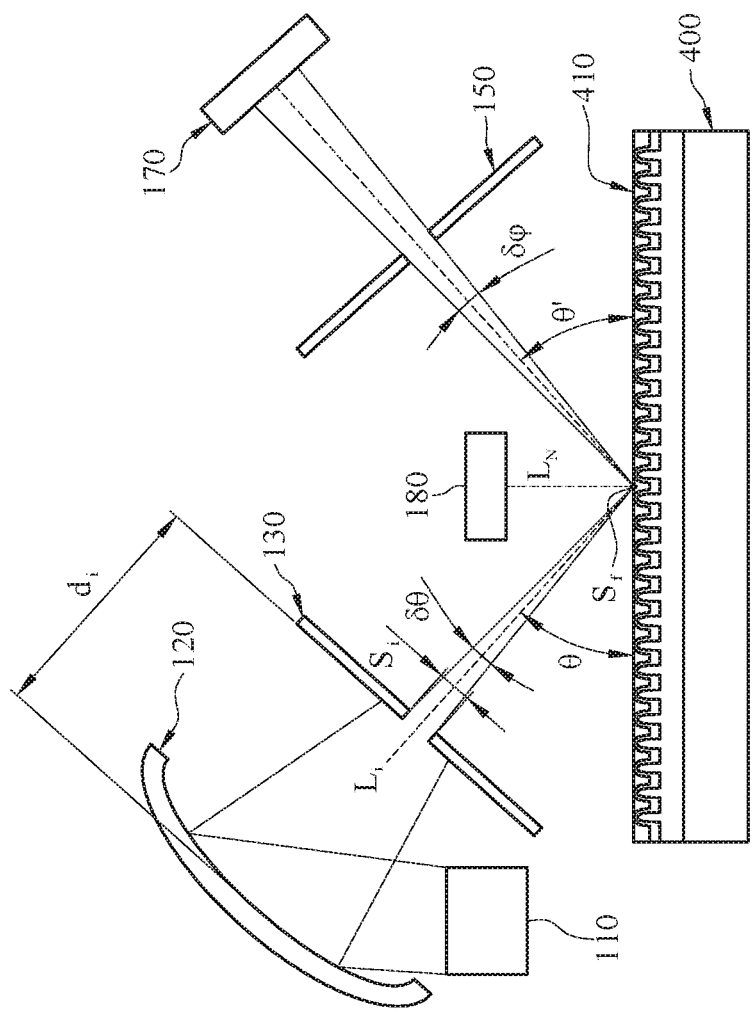
FIG. 1 illustrates an X-ray reflectometry (XRR) apparatus according to one embodiment of the application.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Please refer to FIG. 1, which illustrates an XRR apparatus according to one embodiment of this application. As shown in FIG. 1, the XRR apparatus 100 in one embodiment of the application includes an X-ray source 110, an X-ray reflector 120, a set of incident slits 130, a set of detector slits 150, and an X-ray detector 170. The XRR apparatus 100 is used for analyzing the depth dependent structure of nanostructured surface and/or the film shown as the sample 400.

The X-ray source 110 is capable of generating an X-ray with a wavelength larger than that from a copper anode. The X-ray source 110 includes at least a fine focused anode. In the following embodiments of the application, the anode is a fine focused Aluminum one, but other types of fine focused anodes are also applicable according to the spirit of this application.

The X-ray reflector 120 is used for point focusing the X-ray onto a focal spot $S_f$ on the surface 410 of the sample 400 to enhance the intensity of the X-ray and also to limit the footprint size of the incident X-ray. In one embodiment, the X-ray reflector 120 is made of a curved single crystal monochromator or a multilayer mirror or a combination of both. When the X-ray reflector 120 is manufactured with a multilayer mirror type, the wavelength dispersion of the multilayer mirror is limited to be less than 0.01. The wavelength dispersion is defined as $\delta\lambda/\lambda$, wherein $\lambda$ here refers to the wavelength of the X-ray emitted by the X-ray source 110, and $\delta\lambda$ here refers to the spread of the wavelength of the X-ray after being reflected by the X-ray reflector 120. In some embodiments, the X-ray reflector 120 is a toroidal reflector, a spherical bent quartz (10$\bar{1}$0) monochromator, or a reflective mirror as an illuminating optics for point focusing the X-ray emitted by the fine focused anode to the sample surface 410.

The set of the incident slits 130 is located between the X-ray reflector 120 and the focal spot $S_f$ on the surface 410 of the sample 400 and capable of adjusting the incident angle opening $\delta\theta$. The incident angle opening $\delta\theta$ is defined as an angular spread of the incident X-ray on the plane containing the incident beam $L_i$ and the normal $L_N$ of the surface 410. In one embodiment, the opening $S_i$ of the first set of slits 130 is adjustable. When the opening $S_i$ is enlarged, the incident angle opening $\delta\theta$ is accordingly enlarged. When the opening $S_i$ is reduced, the incident angle opening $\delta\theta$ is accordingly reduced. In another embodiment, the distance $d_i$ between the first set of slits 130 and the X-ray reflector 120 is adjustable. When the distance $d_i$ is reduced, the incident angle opening $\delta\theta$ is accordingly reduced. When the distance $d_i$ is enlarged, the incident angle opening $\delta\theta$ is accordingly enlarged.

When the X-ray is focused onto the focal spot $S_f$, the surface 410 of the sample 400 reflects the point focused X-ray so that the reflected X-ray can be collected by the X-ray detector 170. In one embodiment, the data processor (not shown) of the XRR apparatus 100 is capable of analyzing the data detected by the X-ray detector 170 to deduce or to rebuild the depth dependent information of the nanostructure of the surface 410 of the sample 400. In another embodiment, the processor of the XRR apparatus 100 is capable of analyzing the data of the reflected X-ray detected by the X-ray detector 170 to determine the film-thickness of a film on the surface 410. The above mentioned film thickness and the height of the nanostructure are referred as the characteristic length of the surface 410. In the abovementioned embodiments, the wavelength of the X-ray after the X-ray reflector 120 is no more than twice of the characteristic length of the surface 410. The X-ray detector 170 collects the reflected X-ray on a reflecting path with a reflecting angle $\theta'$ identical to the incident angle $\theta$.

The set of detector slits 150 is located between the X-ray detector 170 and the focal spot $S_f$ on the surface 410 of the sample 400 and capable of adjusting the angle opening $\delta\varphi$ of the reflected X-ray seen by the detector, which is also called the detecting angle opening. The magnitude of the detector angle opening $\delta\varphi$ is similar to that defined by the incident slits 130. In certain embodiments, the detecting angle opening is kept in sync with the incident angle opening $\delta\theta$. However, the detecting angle opening is not necessarily kept in sync with the incident angle opening in other embodiments.

In another embodiment, referring back to FIG. 1, the XRR apparatus 100 further includes an analyzer 180 for collecting the X-ray photoelectron spectrum (XPS) and/or the X-ray fluorescence (XRF) signal(s) when the reflected X-ray is collected. The analyzer 180 in FIG. 1 is located above the surface 410 so as to collect the XPS and the XRF signal(s) to supplement the XRR data. In this embodiment, the processor of the XRR apparatus 100 is capable of collecting/analyzing the structure of the surface 410 of the sample 400 using the XPS, and the XRF data in conjunction with the XRR data.

Figure 2:
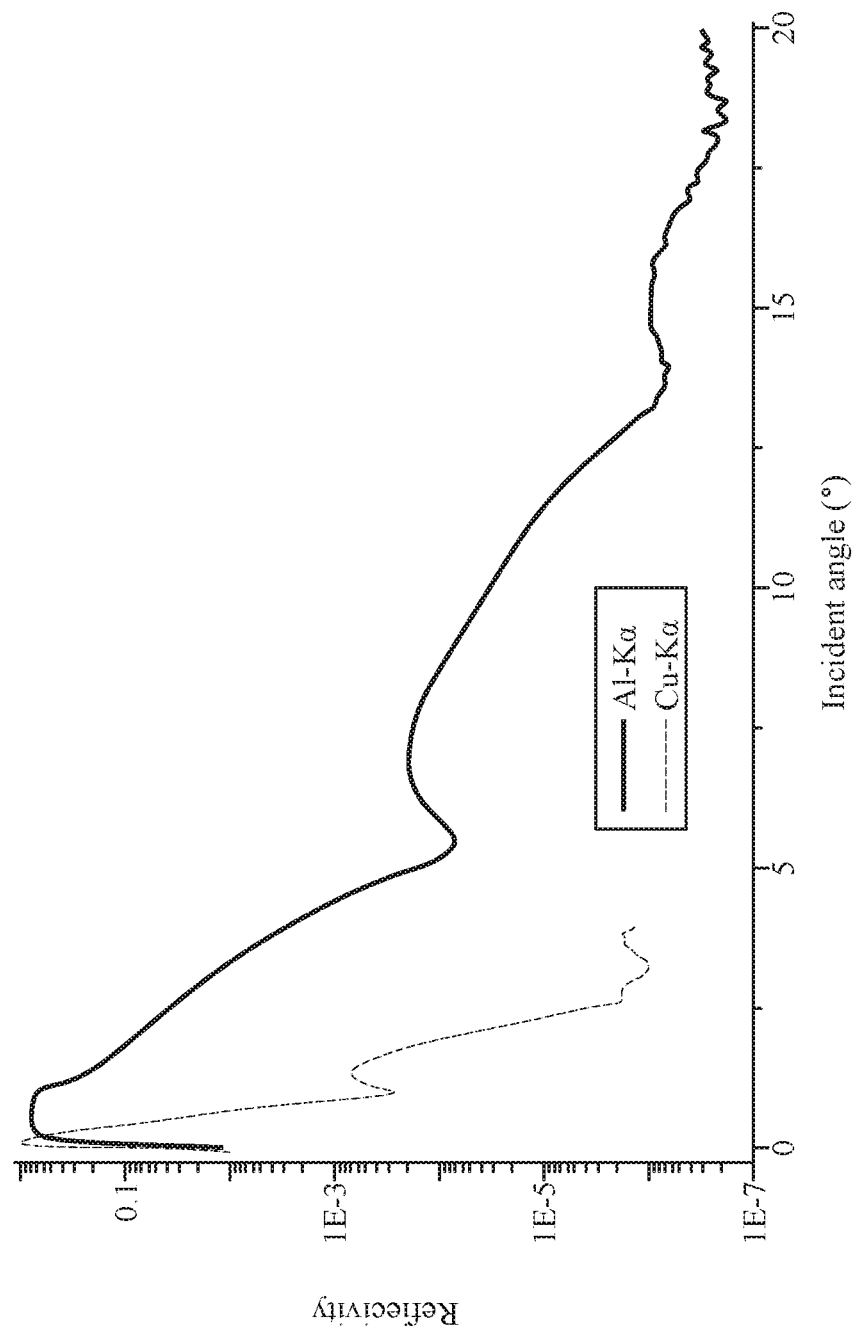
FIG. 2 illustrates a reflectivity-incident angle diagram according to one embodiment of the application.

In one embodiment, referring to FIG. 2, a reflectivity-incident angle diagram measured from a sample 400 composed of a TaN(9 Å)/TiN(10 Å)/HfO$_2$(15 Å) film stack on silicon wafer is given. In the embodiment corresponding to the dash line in FIG. 2 the incident X-ray is at energy of 8.046 KeV, which is close to an example when the fine focused X-ray source 110 is a copper anode and that X-ray is dubbed as Cu—K$_\alpha$. It is shown in FIG. 2 that SNR of the reflectivity of this embodiment degrades when the incident angle $\theta$ is greater than 2.5°. In general, when the Cu—K$_\alpha$ is used for XRR measurements the range of incident angle $\theta$ is between 0° and 4°.

Figure 3:
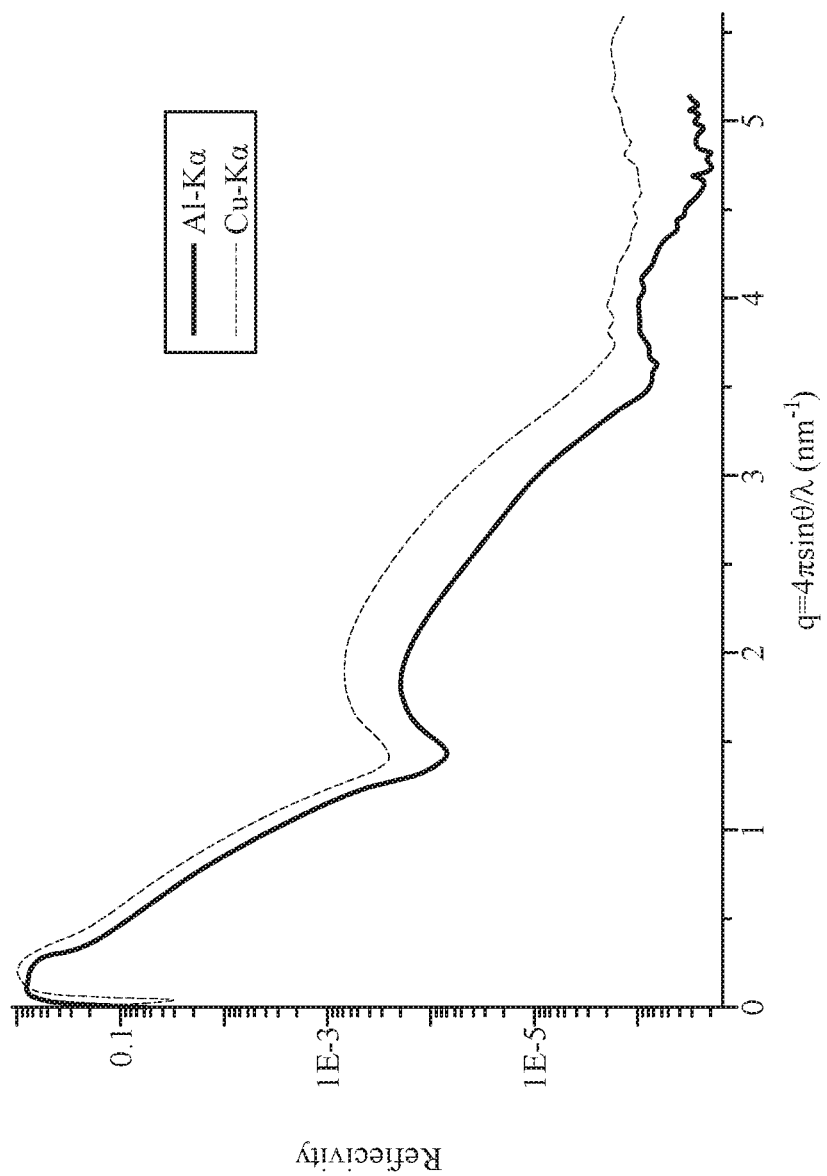
FIG. 3 illustrates the diagram of the relationship between the reflectivity and the wave-vector in one embodiment of the application.

In the embodiment corresponding to the bold line in FIG. 2, the same sample is measured with X-ray at energy of 1.487 KeV, which is close to an example when the fine focused anode in the X-ray source 110 is aluminum and that X-ray is dubbed as Al—K$_\alpha$. It is shown in FIG. 2 that the SNR of the reflectivity of this embodiment degrades when the incident angle $\theta$ is greater than 13°. In general when the Al—K$_\alpha$ is used for XRR measurements the incident angle $\theta$ is between 0° and 20°. The above two data sets re-plotted in q scale yields FIG. 3, both data set have similar characteristics as it should be since the identical sample was used for these measurements. The minor difference between these two curves of FIG. 3 is likely caused by some small differences in the refractive index (n, k) of TaN, TiN, HfO$_2$ and silicon between these two wavelengths.

Now we return to those two important challenges mentioned before when a conventional X-ray reflectivity technique using a short wavelength X-ray such as Cu—K$_\alpha$ at 0.154 nm is applied for samples commonly encountered in semiconductor manufacturing processes. One is the mismatch between the miniscule sample area and the large incident X-ray footprint at low incident angle. When a typical Cu—K$_\alpha$ X-ray source with the wavelength of 0.154 nm is used for the XRR measurements, the incident angle θ of the X-ray is typically scanning between 0° to 4°. The footprint size, denoted as p, on surface 410 of the sample 400 of incident X-ray beam is related to the beam size, denoted as f, by $$p = \frac{f}{\sin\theta}.$$

Under low grazing incident angle θ, a condition necessitated with short wavelength X-ray, an X-ray incident beam with a small beam size f can still result in a footprint too large for test samples with a limited sampling area. For applications in IC chip fabrication a typical sample size is in the range of 40 μm×40 μm. It is therefore advantageous to use X-ray with long wavelength such that the angle range involved is rather large and the factor $$\frac{1}{\sin\theta}$$

decreases, hence, the footprint size p.

The other concern is the measurement time. In order to have sufficient SNR of the reflected X-ray in the high angle range, where the characteristic peaks of thin films appear, the detection time is often be too long to be desirable for IC fabrication applications. It is therefore desirable to enhance the incident X-ray intensity. With long wavelength X-ray the incident intensity can be increased by increasing the incident slit opening to an extent beyond that for short wavelength X-ray at any given q resolution. The above two points will be discussed in more details via the example below.

An example comparison between Al—K$_\alpha$ and Cu—K$_\alpha$ X-ray wavelengths is used to illustrate quantitatively the issues on footprint size as well as intensity enhancement via a large slit opening. The virtual sample for this simulation is a 1 nm thick film on a flat substrate; the first characteristic peak is expected to appear near q=0.628 Å$^{-1}$ and it will be a broad one such as the ones shown in FIG. 3. We choose a q range between 0.428 Å$^{-1}$ to 0.928 Å$^{-1}$ as our region of interest for the rest of discussions. The corresponding angle ranges are from 3° to 6.5° for Cu—K$_\alpha$ at 8.047 KeV and from 16.5° to 38° for Al—K$_\alpha$ at 1.486 KeV, respectively. A high angle region can result in two beneficial effects based on the following analysis. Given that the wave-vector q is defined as equation (1):

$$q = \frac{4\pi\sin\theta}{\lambda} \qquad (1)$$

Please refer to FIG. 3 which illustrates the diagram of the relationship between the reflectivity and the wave-vector in one embodiment of this application. It can be found in FIG. 3 that the relationship between the reflectivity and the wave-vector of the Cu—K$_\alpha$ is similar to that of the Al—K$_\alpha$. This seems to suggest that the user is allowed to choose an X-ray source arbitrarily; however, the following example will demonstrate the merits of choosing long wavelength X-ray for XRR measurements. The resolution of the wave-vector q, denoted as δq/q, can be expressed as a sum of the X-ray wavelength uncertainty and angular uncertainty as shown in equation (2):

$$\frac{\delta q}{q} = \frac{\cos\theta \cdot \delta\theta}{\sin\theta} + \frac{\delta\lambda}{\lambda} \qquad (2)$$

In the equation (2), it is shown that the resolution δq/q is a function of the incident angle θ, the incident angle opening δθ, and the wavelength dispersion δλ/λ. The above equation indicates that to achieve a constant resolution δq/q, i.e. δq/q=c, the incident angle opening δθ of the X-ray should be a function of tan θ, the tangent of the incident angle θ given that the wavelength dispersion δλ/λ stays unchanged. For example, in the case of the lower limit of the incident angle θ, which is 3° for Cu—K$_\alpha$ and 16.5° for Al—K$_\alpha$, this factor (tangent of incident angle θ) is 0.052 for Cu—K$_\alpha$ and 0.296 for Al—K$_\alpha$. In the case of the upper limit of the incident angle θ, which is 6.5° for Cu—K$_\alpha$ and 38° for Al—K$_\alpha$, this factor is 0.114 for Cu—K$_\alpha$ and 0.781 for Al—K$_\alpha$. The abovementioned embodiments demonstrate that the range of the incident angle opening is increased by about 6 times when the X-ray is changed from Cu—K$_\alpha$ to Al—K$_\alpha$. Therefore, the flux of the incident X-ray shall also increase by about 6 times. The above embodiment of the incident angle opening does not imply that the q resolution, defined as δq/q, shall stay unchanged throughout a XRR measurement. In fact, the proportional constant between δθ and tan θ shall depend on other factors including the derivatives of the reflectivity with respect to the incident angle θ. In regions where the reflectivity is expected to have rapid changes with θ the incident angle opening δθ needs to be decreased somewhat to preserve the fidelity of the reflectivity. The local derivatives of the reflectivity with respect to θ are important factors dictating the proportional constant between δθ and tan θ.

In one embodiment, to reduce the size of the footprint is highly desirable and essential for applications where the sampling area is rather limited, e.g. in IC fabrication the typical test area is about 40 μm×40 μm. Taking the X-ray with its size f=10 μm at focal spot $S_f$, the footprint on the surface 410 for the embodiment Cu—K$_\alpha$ varies between $$\frac{10}{\sin 3°} = 191 \text{ μm to } \frac{10}{\sin 6.5°} = 88 \text{ μm}.$$

The corresponding range of footprint for Al—K$_\alpha$ will be between $$\frac{10}{\sin 16.5°} = 35.2 \text{ μm to } \frac{10}{\sin 38°} = 16.2 \text{ μm}$$

The above example demonstrates that high incident flux and small footprint are the two major benefits by using a long wavelength X-ray source. There is an additional intrinsic benefit in applying long wavelength X-ray for XRR as implied by the result given in FIG. 2. The integrated XRR intensity of any scattering peak is scaling linearly with $\lambda$, because that the angular range encompassing any scattering peak is almost proportional to $\lambda$. The integrated peak intensity of an X-ray scattering peak is proportional to the product of the solid angles suspended by the peak and the second power of the amplitude of the structure factor in Fourier space. The structure factor is a constant independent of the probing X-ray wavelength. For a 3D object, its integrated scattering intensity is known to scale as $\lambda^3$. The XRR measurement is along the axis perpendicular to the flat substrate, hence, is a one dimensional measurement the integrated intensity is scaled as $\lambda$.

What is claimed is:

1. An X-ray reflectometry (XRR) apparatus, comprising:
   an X-ray source for emitting an X-ray with a wavelength larger than 0.154 nanometers (nm);
   an X-ray reflector for point focusing the X-ray onto a surface of a sample;
   a set of incident slits between the X-ray reflector and the sample, for adjusting an incident angle opening of the X-ray;
   an X-ray detector for collecting the X-ray reflected by the surface of the sample; and
   a set of detector slits between the X-ray detector and the sample, for controlling a detecting angle opening;
   wherein the X-ray is point focused by the X-ray reflector onto the surface with an incident angle adjustable over a preset range.

2. The XRR apparatus in claim 1, wherein the wavelength is no more than twice of a characteristic length of a structure of the surface.

3. The XRR apparatus in claim 2, wherein the characteristic length is selected from the group consisting of film-thicknesses of the surface and heights of a nanostructure of the surface.

4. The XRR apparatus in claim 1, wherein the X-ray reflector is selected from the group consisting of single crystal monochromators and multilayer mirrors.

5. The XRR apparatus in claim 4, wherein the X-ray reflector is a multilayer mirror type and a wavelength dispersion of the X-ray reflector is less than 0.01.

6. The XRR apparatus in claim 4, wherein the incident angle opening is a function of the incident angle.

7. The XRR apparatus in claim 6, wherein the incident angle opening is a function of a tangent of the incident angle.

8. The XRR apparatus in claim 7, wherein the X-ray source comprises a fine focused Aluminum anode.

9. The XRR apparatus in claim 1, wherein the incident angle opening is a function of the incident angle.

10. The XRR apparatus in claim 9, wherein the incident angle opening is a function of a tangent of the incident angle.

11. The XRR apparatus in claim 1, wherein the X-ray source comprises a fine focused Aluminum anode.

12. The XRR apparatus in claim 1, further comprising at least one analyzer for collecting an X-ray photoelectron spectrum (XPS) and/or an X-ray fluorescence (XRF) signals from the sample during the reflected X-ray is collected by the X-ray detector.

13. A method for X-ray reflectometry (XRR), comprising:
    point focusing an X-ray onto a sample surface with an incident angle, wherein the incident angle is adjustable over a preset range of angles and a wavelength of the X-ray is larger than 0.154 nanometers (nm);
    adjusting an incident angle opening of an incident X-ray according to the incident angle when the incident angle is changed to enhance an incident X-ray flux while keeping a resolution in a desirable range;
    adjusting a detecting angle opening of a reflected X-ray seen by a detector according to a reflection angle when the reflection angle is changed; and
    collecting the X-ray reflected by the sample surface to obtain nanostructure information of the sample surface.

14. The method in claim 13, wherein the wavelength is no more than twice of a characteristic length of a nanostructure on the sample surface.

15. The method in claim 14, wherein the characteristic length is selected from the group consisting of film-thicknesses of the surface and heights of a nanostructure of the surface.

16. The method in claim 13, wherein the incident angle opening is a function of the incident angle.

17. The method in claim 16, wherein the incident angle opening is a function of a tangent of the incident angle.

18. The method in claim 13, further comprising:
    collecting an X-ray photoelectron spectrum (XPS) from the sample during the X-ray reflected by the sample surface is collected; and
    collecting an X-ray fluorescence (XRF) signal corresponding to the sample during the X-ray reflected by the sample surface is collected;
    wherein the nanostructure information of the sample surface is deduced further from the combination of the XPS, the XRF and the XRR signals.

* * * * *

UNITED STATES PATENT AND TRADEMARK OFFICE
CERTIFICATE OF CORRECTION

| | | |
|---|---|---|
| PATENT NO. | : 10,151,713 B2 | Page 1 of 1 |
| APPLICATION NO. | : 15/161046 | |
| DATED | : December 11, 2018 | |
| INVENTOR(S) | : Wu et al. | |

It is certified that error appears in the above-identified patent and that said Letters Patent is hereby corrected as shown below:

On the Title Page

Please insert the heading --Related U.S. Application Data (60)-- and --Provisional application no. 62/165,051, filed on May 21, 2015--.

Signed and Sealed this
Twenty-sixth Day of February, 2019

Andrei Iancu
*Director of the United States Patent and Trademark Office*